United States Patent
Woelfert et al.

(10) Patent No.: US 9,067,872 B2
(45) Date of Patent: Jun. 30, 2015

(54) METHOD FOR COMPRESSING GASES CONTAINING HYDROGEN SULFIDE

(75) Inventors: Andreas Woelfert, Bad Rappenau (DE);
Frank Grzonkowski, Gruenstadt (DE);
Harald Jachow, Bensheim (DE);
Guenter Renz, Freinsheim (DE)

(73) Assignee: BASF SE, Ludwigshafen (DE)

( * ) Notice: Subject to any disclaimer, the term of this patent is extended or adjusted under 35 U.S.C. 154(b) by 1020 days.

(21) Appl. No.: 13/141,906

(22) PCT Filed: Dec. 22, 2009

(86) PCT No.: PCT/EP2009/067739
§ 371 (c)(1),
(2), (4) Date: Jun. 23, 2011

(87) PCT Pub. No.: WO2010/072756
PCT Pub. Date: Jul. 1, 2010

(65) Prior Publication Data
US 2011/0263894 A1    Oct. 27, 2011

(30) Foreign Application Priority Data

Dec. 23, 2008   (EP) .................................... 08172787

(51) Int. Cl.
*C07C 319/02* (2006.01)
*C07C 319/08* (2006.01)
(Continued)

(52) U.S. Cl.
CPC ............. *C07C 319/08* (2013.01); *C07C 303/16* (2013.01); *C07C 319/24* (2013.01)

(58) Field of Classification Search
None
See application file for complete search history.

(56) References Cited

U.S. PATENT DOCUMENTS

| | | | |
|---|---|---|---|
| 2,697,722 A | 12/1954 | Johnson et al. |
| 2,727,920 A | 12/1955 | Johnson et al. |
| 2,820,062 A | 1/1958 | Folkins et al. |

(Continued)

FOREIGN PATENT DOCUMENTS

| | | |
|---|---|---|
| DE | 1 113 446 | 9/1961 |
| DE | 36 10 580 | 10/1986 |

(Continued)

OTHER PUBLICATIONS

"Hydrogen Sulfide" in Ullmann's Encyclopedia of Industrial Chemistry, 6th Edition, 2003, vol. 17, pp. 285-305.*

(Continued)

*Primary Examiner* — Karl J Puttlitz
(74) *Attorney, Agent, or Firm* — Oblon, McClelland, Maier & Neustadt, L.L.P.

(57) ABSTRACT

A process for compressing a hydrogen-sulfide-comprising gas stream, which comprises
(i) compressing the hydrogen-sulfide-comprising gas stream in a compressor,
(ii) flushing the compressor with a mixture comprising dialkyl polysulfides, dialkyl disulfides and at least one amine;
a process for producing sulfur compounds, selected from the group consisting of alkylmercaptans, dialkyl disulfides and alkanesulfonic acids, which comprises the conversion of hydrogen-sulfide-comprising gas streams, wherein the hydrogen-sulfide-comprising gas streams are compressed according to the process comprising steps i) and ii); and also the use of a mixture comprising dialkyl polysulfides, dialkyl disulfides and at least one amine for removing sulfur deposits which occur in the compression of hydrogen-sulfide-comprising gas streams.

20 Claims, 1 Drawing Sheet

(51) Int. Cl.
*C07C 303/16* (2006.01)
*C07C 319/24* (2006.01)

(56) References Cited

U.S. PATENT DOCUMENTS

| | | | |
|---|---|---|---|
| 2,822,401 | A | 2/1958 | Hoot et al. |
| 2,863,725 | A | 12/1958 | Maude et al. |
| 2,874,129 | A | 2/1959 | Bell et al. |
| 4,248,717 | A | 2/1981 | Sharp et al. |
| 5,847,223 | A | 12/1998 | Ponceblanc et al. |
| 5,852,219 | A | 12/1998 | Sauer et al. |
| 5,874,630 | A | 2/1999 | Cook et al. |
| 5,886,230 | A * | 3/1999 | Hofen et al. ............... 568/71 |
| 6,531,629 | B1 | 3/2003 | Eiermann et al. |
| 6,686,506 | B1 | 2/2004 | Hesse et al. |
| 7,887,777 | B2 | 2/2011 | Wolfert et al. |
| 7,927,080 | B2 * | 4/2011 | Muller et al. ............... 417/53 |
| 2005/0265913 | A1 | 12/2005 | Moller et al. |

FOREIGN PATENT DOCUMENTS

| | | | |
|---|---|---|---|
| DE | 3610580 | * | 10/1986 |
| DE | 196 39 584 | | 4/1998 |
| DE | 196 54 515 | | 10/1998 |
| DE | 198 54 427 | | 5/2000 |
| DE | 10137773 | * | 8/2001 |
| DE | 101 16 817 | | 10/2002 |
| DE | 101 37 773 | | 2/2003 |
| DE | 102 45 164 | | 4/2004 |
| EP | 0 038 540 | | 10/1981 |
| EP | 0 564 706 | | 10/1993 |
| EP | 0 749 961 | | 12/1996 |
| EP | 0 850 922 | | 7/1998 |
| EP | 1 005 906 | | 6/2000 |
| WO | 98 34914 | | 8/1998 |
| WO | 00 31027 | | 6/2000 |
| WO | 2004 022482 | | 3/2004 |
| WO | 2008 087125 | | 7/2008 |

OTHER PUBLICATIONS

International Search Report Issued Apr. 29, 2010 in PCT/EP09/067739 filed Dec. 22, 2009.
"Hydrogen Sulfide" Ullmann'S Encyclopedia of Industrial Chemistry, 7$^{th}$ Edition, Total 21 Pages, (2008).
"Hydrogen Sulfide" Ullmann'S Encyclopedia of Industrial Chemistry, 6$^{th}$ Edition, vol. 17, Total 23 Pages, (2003).
Zimmermann. K. T. et al., "Schwefelwasserstoff-Entwickler Fuer Das Laboratorium", Angew. Chem, vol. 74, No. 4, p. 151, (1962).
"Production Challenges in Developing Sour Gas Reservoirs", Chemical Engineering World, vol. 24, No. 3, pp. 87-93, (Mar. 1989).

* cited by examiner

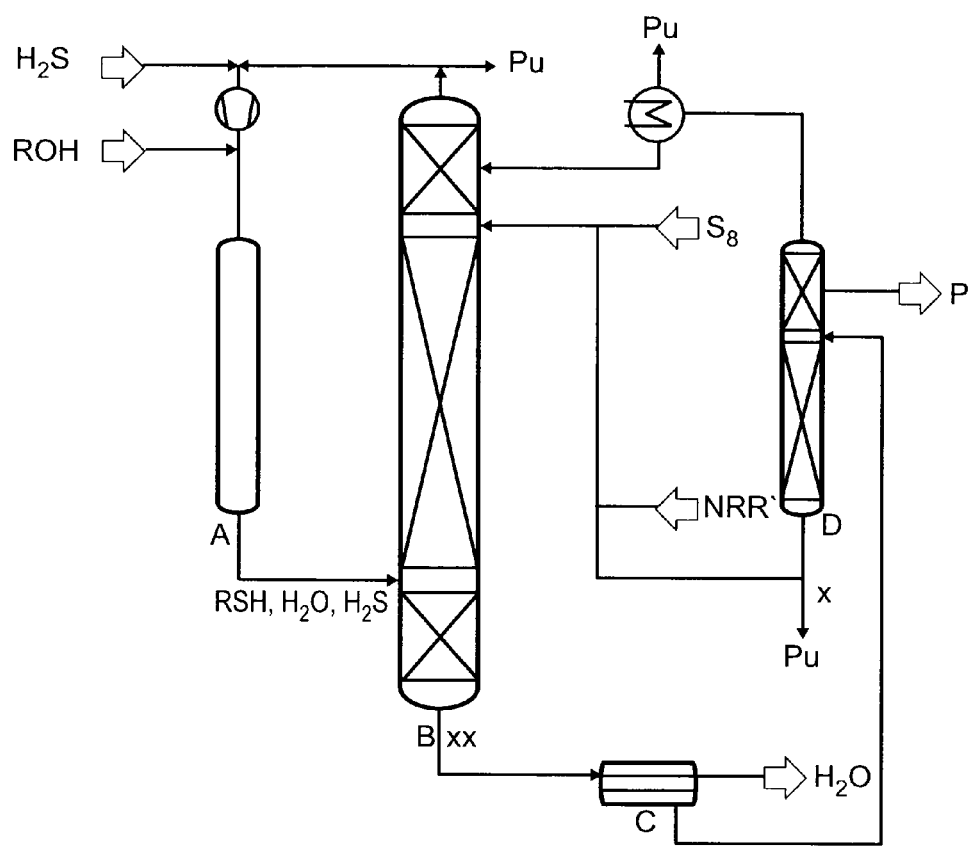

METHOD FOR COMPRESSING GASES CONTAINING HYDROGEN SULFIDE

The present invention relates to a process for compressing a hydrogen-sulfide-comprising gas stream, which comprises
(i) compressing the hydrogen-sulfide-comprising gas stream in a compressor,
(ii) flushing the compressor with a mixture comprising dialkyl polysulfides, dialkyl disulfides and at least one amine;

a process for producing sulfur compounds, selected from the group consisting of alkylmercaptans, dialkyl disulfides and alkanesulfonic acids, which comprises the conversion of hydrogen-sulfide-comprising gas streams, wherein the hydrogen-sulfide-comprising gas streams are compressed according to the process comprising steps i) and ii); and also the use of a mixture comprising dialkyl polysulfides, dialkyl disulfides and at least one amine for removing sulfur deposits which occur in the compression of hydrogen-sulfide-comprising gas streams.

The compression of hydrogen-sulfide-comprising gas streams is a frequent processing problem. Hydrogen sulfide is frequently used under pressure. Thus, for example, the precipitation of heavy metals from solution is carried out under pressure. As a result, precipitation apparatuses having a small volume can be used. In addition, the synthesis of alkylmercaptans by reacting hydrogen sulfide with alkanols is customarily carried out using compressed hydrogen sulfide. The alkylmercaptans can subsequently be further reacted, eg. to form dialkyl sulfides and/or alkanesulfonic acids.

The hydrogen sulfide used in the abovementioned processes can, for example, be obtained from an acid gas scrubber, from refinery processes or by reaction of the elements sulfur and hydrogen. Because of the toxicity of the hydrogen sulfide, attempts are made to keep not only the amount of hydrogen sulfide which is handled in a production process, but also the pressure at which the hydrogen sulfide is handled, as small as possible. Therefore the hydrogen sulfide is customarily as far as possible produced or provided at atmospheric pressure and not compressed until the application stage.

In the compression of hydrogen-sulfide-comprising gas streams, it is frequently observed that the compressor becomes blocked with sulfur deposits. These can lead to a fall in compressor performance or, if the compressor is operated further despite deposits, to mechanical damage on the compressor.

One cause of the sulfur deposits is the entrainment of elemental sulfur from the hydrogen-sulfide-comprising source used, which sulfur deposits, in particular, on cold surfaces. A further cause is the decomposition of polysulfanes ($H_2S_x$, in particular to hydrogen sulfide and sulfur) which are generally present in the hydrogen-sulfide-comprising source.

An essential factor for the availability of production plants for synthesizing alkylmercaptans and/or dialkyl disulfides and sulfonic acids produced therefrom is therefore the availability of the compressor for the hydrogen-sulfide-comprising gas.

One possible method of increasing the availability of the compressor is the purification of hydrogen-sulfide-comprising gases before introduction into the compressor.

For instance WO 2004/022482 relates to the purification of hydrogen sulfide by porous media. According to WO 2004/022482, hydrogen-sulfide-comprising gas obtained by reacting hydrogen and liquid sulfur is passed for purification through a filter which comprises a solid selected from activated carbon, aluminum oxide and silicon dioxide. According to WO 2004/022482, the gas thus purified is capable of depositing solid sulfur only to a slight extent, or not at all.

DE 102 45 164 A1 relates to a process for the conversion of polysulfanes. These polysulfanes $H_2S_x$ occur in the synthesis of hydrogen sulfide by reaction of hydrogen with sulfur. On compression of the hydrogen-sulfide-comprising gas stream, an uncontrolled decomposition of the polysulfanes to hydrogen sulfide and sulfur occurs, which leads to unwanted sulfur deposits in the entire compression zone. According to DE 102 45 164 A1, the polysulfanes in the hydrogen-sulfide-comprising gas from the synthesis by reaction of hydrogen and sulfur are catalytically converted to hydrogen sulfide and sulfur by bringing the hydrogen-sulfide-comprising gas into contact with catalytically active solids, catalytically active liquids or gases. Suitable catalytically active solids are, according to DE 102 45 164 A1, activated carbon, $Al_2O_3$, $SiO_2$, zeolites, glasses, oxides and mixed oxides, alkali metal, alkaline earth metal and other basic mixtures or hydroxides. Suitable catalytically active liquids are basic, aqueous or alcoholic solutions of ammonia, amines or aminoalcohols, and also solutions of alkali metal, alkaline earth metal or other basic oxides or hydroxides, sulfides or hydrogensulfides. Suitable gases are ammonia, amines or aminoalcohols.

A disadvantage of the abovementioned processes for purifying the hydrogensulfide obtained from the reaction of hydrogen with sulfur is the lasting consumption of the components used for the purification.

As an alternative, it is proposed to remove the sulfur-comprising impurities in hydrogen-sulfide-comprising gases by condensation or desublimation in heat exchangers operating in alternation which can then be freed from sulfur deposits by heating, when required (see Ullmann's Encyclopedia of Industrial Chemistry, Release 2008, 7th Edition, DOI: 10.1002/14356007.a13_467, chapter "Hydrogen Sulfide", section "4.1 Production by chemical reaction").

In principle, furthermore, mechanical cleaning of the compressor of hydrogen sulfide deposits is possible. However, this is always associated with an opening of the plant and potential emission of hydrogen sulfide. Furthermore, the opening of the plant in the case of plants having toxic media is associated with long shutdown times because of the preceding cleaning processes.

The object of the present invention is therefore providing a process for compressing hydrogen-sulfide-comprising gases having the highest possible availability with respect to the compressor, which process succeeds with the lowest capital expenditure possible.

This object is achieved by a process for compressing a hydrogen-sulfide-comprising gas stream, which comprises
i) compressing the hydrogen-sulfide-comprising gas stream in a compressor,
ii) flushing the compressor with a mixture comprising dialkyl polysulfides, dialkyl disulfides and at least one amine.

Step i)

A "compressor", for the purposes of the present invention, is to be taken to mean not only the compressor itself but also its peripherals, that is to say, in particular, the compressor and one or more attached heat exchangers, e.g. shell and tube or plate heat exchangers, and also, if appropriate, attached liquid separators.

As compressors in the present process, in principle all compressors known to those skilled in the art are suitable. Preferably, in the process according to the present invention, use is made of rotary gas compressors, particularly preferably screw compressors, or liquid ring compressors, wherein liquid ring compressors are very particularly preferred. Rotary gas compressors, in particular screw compressors and liquid ring compressors, are known to those skilled in the art.

The screw compressor falls under the rotary twin-shaft displacement compressors having internal compression. The screw compressor can have a single-stage or two-stage construction. For cooling the hydrogen-sulfide-comprising gas stream which is to be compressed, during the compression, an injection medium can be sprayed in. The injection can proceed upstream of the first and/or second stage. As injection medium, use can be made of, for example, water or an alcohol (for example methanol in the production of methylmercaptan). The injection medium vaporizes in part or completely during the injection and compression process and thereby cools the process gas. After the compression, the injection medium can be condensed or left in the process gas (one example for compression in the screw compressor using methanol as injection medium is disclosed, for example, in DE-A 196 54 515). In the case of condensation of the injection medium and/or cooling, it can be used again as injection medium, if appropriate after filtration.

The liquid ring compressor which is particularly preferably used in the process according to the invention is a rotary displacement compressor of single-shaft type. The ring liquid used in the liquid ring compressor used according to the process according to the invention can be, for example, water or the mixture which is used according to the invention for flushing the compressor and comprises dialkyl polysulfides, dialkyl disulfides and at least one amine. In a preferred embodiment, water is used as ring liquid. Ring liquid entrained in the compression process is separated off in a liquid separator (demistor, apparatus for separation of gas and liquid) after it leaves the compressor, passed through a heat exchanger for cooling and from there conducted back into the compressor. Suitable heat exchangers are, for example, shell and tube heat exchangers or plate heat exchangers. In the case of the liquid ring compressor, the sulfur deposits occur on compression of the hydrogen-sulfide-comprising gas stream in particular in the liquid ring compressor itself and also in the heat exchanger or heat exchangers.

The compression in step i) of the process according to the invention can proceed in a single stage, two-stage or multi-stage manner. Preferably, the compression proceeds in a single or two-stage manner.

A compressor which has no sulfur deposits generally has a compressor output which is so high that more gas is compressed than is needed for the subsequent step. The excess compressed gas is recirculated via a bypass around the compressor from the pressure side to the suction side of the compressor (and fed back to the compressor). In the case when the compressor is blocked with sulfur deposits, the compressor output decreases with the amount of sulfur deposits in the compressor. This means that less gas is recirculated to the compressor via the bypass. If the compressor output is so low owing to the sulfur deposits that no gas is recirculated any more via the bypass, the compressor must be flushed.

Operating Conditions of the Compressor

The entry pressure into the compressor is generally 700 mbar to 3000 mbar absolute, preferably 1000 to 2000 mbar absolute, particularly preferably 1100 to 1500 mbar absolute. The exit pressure from the compressor is generally 1000 to 7000 mbar absolute, preferably 1500 to 4000 mbar absolute, particularly preferably 2000 to 3200 mbar absolute, very particularly preferably 2200 to 2800 mbar absolute, wherein the entry pressure is lower than the exit pressure. The pressure conditions in the compressor used in the process according to the invention differ thereby substantially from the pressure conditions in a borehole in which pressures of about 80 bar customarily prevail.

The entry temperature into the compressor is generally 10 to 70° C., preferably 15 to 50° C., particularly preferably 20 to 30° C. The exit temperature from the compressor is generally 15 to 200° C., preferably 20 to 100° C., particularly preferably 25 to 50° C., very particularly preferably 30 to 40° C. Generally, the entry temperature is lower than the exit temperature.

Hydrogen-Sulfide-Comprising Gas Stream

The hydrogen-sulfide-comprising gas stream passed through the compressor can be produced by any process known to those skilled in the art. The gas stream can originate either from the acid gas scrubber or from refinery processes or can be obtained from the elements sulfur and hydrogen. Preferably, the hydrogen-sulfide-comprising gas stream is produced from the elements sulfur and hydrogen in the presence of a catalyst, or non-catalytically. Suitable processes for producing the hydrogen-sulfide-comprising gas stream are known to those skilled in the art.

By way of example, a hydrogen-sulfide-comprising gas stream is produced according to the prior art by the $H_2S$ process of Girdler (Ullmann's Encyclopedia of Industrial Chemistry, 6th Edition, 2003, Vol. 17, page 291). In this process, $H_2S$ is produced non-catalytically from the elements sulfur and hydrogen in a column having internals and in an essentially horizontally directed expanded bottom phase. Into the bottom phase which is filled with boiling sulfur, hydrogen is introduced which strips into the ascending gas phase. Hydrogen and ascending sulfur react in the gas space of the column, wherein the heat of reaction thus liberated is removed from the product gas by scrubbing with liquid sulfur. For this, liquid sulfur is taken off from the bottom phase of the column, mixed with fresh cold sulfur and applied to the top of the column. The product gas, which comprises substantially hydrogen sulfide, is cooled in two heat exchangers.

A catalytic production of hydrogen sulfide is described, for example, in Angew. Chem., Volume 74, 1962; No. 4; page 151. In this process, hydrogen is passed into an externally heated sulfur bath. The hydrogen loaded with sulfur vapor enters through boreholes into a catalyst space. Incompletely reacted sulfur is, after it leaves the catalyst space, condensed in an upper part of the hydrogen sulfide outlet tube and passes back into the sulfur bath via a return tube. The catalyst space is arranged concentrically around the hydrogen sulfide outlet tube.

Other examples of a catalytic production of hydrogen sulfide from the elements sulfur and hydrogen are described in DE 1 113 446 and U.S. Pat. No. 2,863,725.

DE 1 113 446 describes the catalytic production of hydrogen sulfide by reaction of a stoichiometric mixture of hydrogen and sulfur in the presence of a cobalt and molybdenum salt on a support comprising catalyst at temperatures below 500° C., preferably between 300 and 400° C. The catalyst in this case is arranged in tubes through which the mixture of hydrogen and sulfur flows.

According to U.S. Pat. No. 2,863,725 hydrogen sulfide is produced from hydrogen and sulfur in the presence of a molybdenum-comprising catalyst, wherein gaseous hydrogen is passed into a reactor comprising a sulfur melt and ascends through the sulfur melt in the form of gas bubbles.

The sulfur-comprising gas stream is customarily produced at pressures of 0.7 to 2 bar, preferably 0.9 to 1.5 bar, very particularly preferably 1 bar to 1.4 bar absolute.

The temperature of the hydrogen-sulfide-comprising gas stream obtained after the production is generally 10 to 60° C., preferably 15 to 50° C., particularly preferably 20 to 45° C., very particularly preferably 25 to 40° C.

In the case of the syntheses of hydrogensulfide from hydrogen and sulfur, polysulfanes ($H_2S_x$) are generally found as by-products in the hydrogen-sulfide-comprising crude gas stream, obtained in an amount of generally 10 to 200 ppm by weight, preferably 15 to 100 ppm by weight, particularly preferably 20 to 75 ppm by weight, very particularly preferably 25 to 50 ppm by weight.

The polysulfanes are removed from the hydrogen-sulfide-comprising gas stream preferably before carrying out the process according to the invention for compressing the hydrogen-sulfide-comprising gas stream. This can proceed, for example, by one of the processes described in the abovementioned documents WO 2004/022482 or DE 102 45 164 A1. It is likewise possible to purify the polysulfanes by passing them through a porous material (activated carbon filter or molecular sieve), for example as disclosed in WO 2008/087125.

In addition, in a preferred embodiment, a further prepurification of the hydrogen-sulfide-comprising gas stream proceeds by desublimation in a heat exchanger. The gas leaving the desublimator has preferably a molecular sulfur fraction of 0.001 to 5 ppm by weight, particularly preferably 0.005 to 2 ppm by weight, very particularly preferably 0.01 to 1 ppm by weight.

The purity of the hydrogensulfide (hydrogen-sulfide-comprising gas stream) used in the process according to the invention for compression is generally 90 to 99.9% by volume, preferably 95 to 99.8% by volume, particularly preferably 98 to 99.7% by volume, and very particularly preferably 99 to 99.6% by volume.

Step ii)

Step ii) according to the invention comprises flushing the compressor with a mixture comprising dialkyl polysulfides, dialkyl disulfides and at least one amine.

The use of dialkyl polysulfides as solvent for dissolution of sulfur deposits in lines which serve for the transport of sulfur-comprising materials, in particular deposits in the extraction of natural gas from high-sulfur natural gas sources, is known to those skilled in the art, for example from DE 36 10 580 A1. There, a process is described for dissolving sulfur by means of a liquid dialkyl polysulfide, wherein the solvent comprises a dimethyl polysulfide mixture comprising 1 to 3% by weight of dimethyl disulfide, 35 to 45% by weight of $CH_3S_xCH_3$, wherein x has a value from 3 to 5, and the remainder homologous polysulfides, wherein x has a value of 6 or more and in particular 6 to 8. In addition, the dialkyl polysulfide used can comprise 2 to 10% by weight of an amine, amide, mercaptan and/or mercaptide. The solvent disclosed in DE 36 0 580 A1 serves for dissolving sulfur deposits which can occur in lines which serve for the transport of sulfur-comprising materials. In this case the problem of sulfur sedimentation is of particular importance according to DE 36 10 580 A1 in high-sulfur natural gas sources, wherein the high sulfur-content gases lead to sulfur deposits on the inner walls of the pipelines. According to DE 36 10 580 A1, dimethyl disulfide (DMDS) has a considerable dissolving power for sulfur. Since it is necessary for continuous cleaning that the composition of the solvent used remains substantially constant, it is necessary to regenerate the dimethyl disulfide customarily used in the prior art by breaking down the higher polysulfides taken up during the cleaning. According to DE 36 10 580 A1, it has been found that as alternative to dimethyl disulfide, use can be made of dimethyl polysulfide mixtures having the special abovementioned composition for removing sulfur deposits in lines with serve for the transport of sulfur-comprising materials.

However, whereas DE 36 10 580 A1 relates to a process for dissolving sulfur in lines which conduct the hydrogen-sulfide-comprising gases from high-sulfur natural gas sources, the present invention relates to a process for compressing hydrogen-sulfide-comprising gases, which comprises flushing the compressor with a mixture comprising dialkyl polysulfides, dialkyl disulfides and at least one amine. The temperature and pressure conditions which prevail in the lines according to DE 36 10 580 A1, and also the hydrogen-sulfide-comprising gas streams used differ considerably from the conditions occurring in the compression of hydrogen-sulfide-comprising gases and the hydrogen-sulfide-comprising gas streams used. In addition, the devices on which the sulfur deposits are observed are also different. Whereas DE 36 10 580 A1 relates to the problems of sulfur deposition in pipelines, the present application relates to the problem of sulfur deposits in compressors, which also include the peripherals of the compressor, for example heat exchangers. The compressors and, in particular, the heat exchangers which are attached to the compressors are distinguished in that they have narrow gaps. A person skilled in the art would use low-viscosity flushing solutions for cleaning the gaps.

The suitability of mixtures which comprise dialkyl polysulfides, dialkyl disulfides and at least one amine for flushing the compressor is therefore not obvious in the knowledge of DE 36 10 580 A1, in particular for the following reasons:

In boreholes, pressures of about 80 bar generally prevail, whereas the compressor is generally operated at an entry pressure of 700 mbar to 3000 mbar absolute and an exit pressure of 1000 to 7000 mbar absolute.

In addition, the structural conditions in boreholes, wherein these are generally tubes of several cm in diameter, differ significantly from the structural conditions of a compressor and peripherals thereof, which generally has narrow gaps in the mm range.

These differences lead to the fact that a person skilled in the art would not use, for flushing a compressor and peripherals thereof, the high-viscosity mixtures according to DE 36 10 580 A1 which are suitable for flushing boreholes, since these high-viscosity mixtures, under the pressure conditions prevailing in the compressor, can pass only with difficulty into the narrow gaps of the compressor and likewise can be washed out again with difficulty.

Therefore, a person skilled in the art, would rather use the essentially lower-viscosity solutions containing dialkyl disulfides for flushing the compressor, which are customarily used for removing sulfur deposits in boreholes, as found in the publication "Production challenges in developing sour gas reserves", Chemical Engineering World 24(3), 87-93, Hyne. J. B., where dimethyl disulfide is shown to the best solvent for sulfur (page 91) in the application in sour gas boreholes.

The dialkyl disulfides customarily used for removing sulfur deposits in boreholes, however, surprisingly proved not to be very suitable for the rapid and lasting removal of sulfur deposits in a compressor, as the comparative examples in the present application show. Surprisingly, it has been found that with the mixture used according to the invention comprising dialkyl polysulfides, dialkyl disulfides and at least one amine, despite the high viscosity, significantly better results are achieved for the rapid and lasting removal of sulfur deposits in a compressor.

Moreover, the different pressure and temperature conditions in the pipelines according to DE 36 10 580 A1 and in the compressor according to the present application have the effect that the sulfur deposits in the respective devices can have different modifications. Different sulfur modifications display a markedly differing solution behavior. Rhombic sulfur $S_8$, for example, exhibits a significantly higher reactivity and solubility than what is termed μ sulfur. It is known that rapid subcooling on cold surfaces, for example on heat-exchange surfaces, leads to μ sulfur. The type of sulfur deposition and therefore the solubility of the sulfur deposits depends essentially on the temperature history and the origin of the hydrogen-sulfide-comprising gas from which the sulfur deposits result. Experience on removal of sulfur deposits from a hot borehole therefore cannot be readily applied to the removal of sulfur deposits in a compressor. These are two completely different technical fields.

Flushing the compressor according to step ii) of the process according to the invention can proceed continuously or discontinuously.

In the case of continuous flushing, the compressor is freed continuously from the sulfur deposits using the mixture used according to the invention comprising dialkyl polysulfides, dialkyl disulfides and at least one amine. In this case, the mixture used according to the invention is added, e.g., when a liquid ring compressor is used, to the ring liquid which is recirculated to the compressor. A continuous procedure of the process according to the invention when other compressors are used is possible without problem for a person skilled in the art on the basis of his knowledge. The pressure and temperature conditions in the compressor in the case of the continuous procedure correspond to the abovementioned pressure and temperature conditions in the compressor.

In the case of the discontinuous flushing, the compressor is shut down for a short time for cleaning work and treated using the mixture used according to the invention comprising dialkyl polysulfides, dialkyl disulfides and at least one amine.

Customarily, the discontinuous flushing of the compressor with the mixture used according to the invention comprising dialkyl polysulfides, dialkyl disulfides and at least one amine proceeds in the form that the mixture in liquid form flows through the compressor. The temperature in the flushing operation is generally 30 to 160° C., preferably 40 to 140° C., particularly preferably 60 to 120° C., very particularly preferably 75 to 110° C., and especially very particularly preferably 90 to 100° C.

In the case of discontinuous flushing, the compressor is filled in part or completely with the mixture used for the flushing. Preferably, the filling is complete. In the case of discontinuous flushing the flushing times are from 5 minutes to 1 hour, preferably 10 minutes to 50 minutes, particularly preferably 20 minutes to 40 minutes.

Dialkyl Disulfides and Dialkyl Polysulfides

Suitable alkyl groups of the dialkyl disulfides and dialkyl polysulfides are, independently of one another in each dialkyl disulfide and/or dialkyl polysulfide, customarily $C_1$-$C_{14}$ alkyl moieties, preferably $C_1$-$C_6$ alkyl moieties, particularly preferably $C_1$-$C_3$ alkyl moieties. Very particularly preferably the alkyl moieties are methyl, ethyl, n-propyl or isopropyl, very particularly preferably the alkyl moieties are methyl moieties. The alkyl moieties in the dialkyl polysulfides and/or dialkyl disulfides can in each case be identical or different. Preferably, they are identical. Particularly preferably the dialkyl polysulfides used in the process according to the invention are dimethyl polysulfides and the dialkyl disulfides are dimethyl disulfide.

Suitable dialkyl polysulfides have the general formula R—$S_x$—R', wherein R and R' are the abovementioned alkyl moieties. x in the dialkyl polysulfides means 3 to 12, preferably 3 to 10. Customarily, the dialkyl polysulfides are present in the form of mixtures of dialkyl polysulfides having various chain lengths.

Amines

The at least one amine which is comprised in the mixture used in step ii) according to the invention for flushing can be a primary, secondary or tertiary aliphatic or aromatic amine. Preferably, use is made of primary, secondary or tertiary aliphatic amines. Particular preference is given to liquid or solid amines which have a low water solubility. Very particularly preferably the amines are primary, secondary or tertiary amines having 6 to 60 carbon atoms. Examples of suitable amines are tridecylamine, fatty amines such as N,N-dimethyl-$C_{12}$/$C_{14}$-amine, and also dicyclohexylamine.

The mixtures which are used according to the invention in step ii) for flushing and which comprise dialkyl polysulfides, dialkyl disulfides and at least one amine, in a preferred embodiment, comprise a) 10 to 98% by weight, preferably 20 to 95% by weight, particularly preferably 35 to 90% by weight, of dialkyl polysulfides;

b) 1.9 to 80% by weight, preferably 4.8 to 72% by weight, particularly preferably 9.5 to 60% by weight, of dialkyl disulfides;

c) 0.1 to 10% by weight, preferably 0.2 to 8% by weight, particularly preferably 0.5 to 5% by weight, of at least one amine;

wherein the sum of dialkyl polysulfides, dialkyl disulfides and at least one amine totals 100% by weight.

Preferred dialkyl polysulfides, dialkyl disulfides and amines are mentioned hereinbefore.

Depending on whether the flushing in step ii) of the process for compression according to the invention is carried out continuously or discontinuously, the composition of the dialkyl polysulfide containing mixture which is preferably used can vary.

In a preferred embodiment of step ii) of the process according to the invention, use is made of mixtures comprising:

a) 50 to 98% by weight, preferably 70 to 95% by weight, particularly preferably 80 to 90% by weight, of dialkyl polysulfides;

b) 1.9 to 40% by weight, preferably 4.8 to 22% by weight, particularly preferably 9.5 to 15% by weight, of dialkyl disulfides;

c) 0.1 to 10% by weight, preferably 0.2 to 8% by weight, particularly preferably 0.5 to 5% by weight, of at least one amine;

wherein the sum of dialkyl polysulfides, dialkyl disulfides and at least one amine totals 100% by weight.

The mixture mentioned above is used particularly preferably when step ii) of the process according to the invention is carried out discontinuously.

In a further preferred embodiment of step ii) of the process according to the invention, use is made of mixtures comprising:

a) 10 to 70% by weight, preferably 20 to 60% by weight, particularly preferably 35 to 50% by weight, of dialkyl polysulfides;

b) 29.9 to 80% by weight, preferably 38.8 to 72% by weight, particularly preferably 49.5 to 60% by weight, of dialkyl disulfides;

c) 0.1 to 10% by weight, preferably 0.2 to 8% by weight, particularly preferably 0.5 to 5% by weight, of at least one amine;

wherein the sum of dialkyl polysulfides, dialkyl disulfides and at least one amine totals 100% by weight.

The mixture mentioned above is used particularly preferably when step ii) of the process according to the invention is carried out continuously.

The mixture used in step ii) can in addition comprise small amounts of other components, for example small amounts of alkylmercaptan and hydrogen sulfide. In a preferred embodiment, the mixtures, in addition to the abovementioned small amounts present if appropriate of alkylmercaptan and hydrogen sulfide, do not contain any other components. In particular, the mixtures used for flushing, in a preferred embodiment of the present invention, do not comprise surfactants.

In a preferred embodiment of the present invention, the mixtures used for flushing the compressor in step ii) are not mixtures which must be prepared extra for the purpose of flushing, but are mixtures as are obtained in processes for producing sulfur compounds starting from hydrogen-sulfide-comprising gas compressed according to the process according to the invention. Such sulfur compounds are, for example, alkylmercaptans, dialkyl disulfides and alkanesulfonic acids. Particularly preferably, the mixtures used for the flushing in step ii) of the process according to the invention are the amine-containing crude discharge from the dialkyl disulfide synthesis which can be carried out according to processes known to those skilled in the art and will be described in more detail hereinafter.

The process according to the invention for compressing a hydrogen-sulfide-comprising gas stream, in one embodiment of the present invention, is used in combination with the production of sulfur compounds, in particular sulfur compounds selected from the group consisting of alkylmercaptans, dialkyl disulfides and alkanesulfonic acids. Therefore, the present invention further relates to a process for producing sulfur compounds, selected from the group consisting of alkylmercaptans, dialkyl disulfides and alkanesulfonic acids, which comprises the conversion of a hydrogen-sulfide-comprising gas stream, wherein the hydrogen-sulfide-comprising gas stream is compressed according to the process according to the invention for compressing the hydrogen-sulfide-comprising gas stream which comprises steps i) and ii).

Processes for Producing Alkylmercaptans

Processes for producing alkylmercaptan are known to those skilled in the art. According to the invention, for producing the alkylmercaptans, use is made of a compressed hydrogen-sulfide-comprising gas stream, wherein the compression of the hydrogen-sulfide-comprising gas stream used for the production of the alkylmercaptans comprises the steps i) and ii). Preferably, the alkylmercaptans are produced by reacting alkanols with a hydrogen-sulfide-comprising gas stream which is compressed according to the process according to the invention comprising the steps i) and ii).

The present invention therefore further relates to a process for producing alkylmercaptans, which comprises the steps:
i) compressing the hydrogen-sulfide-comprising gas stream in a compressor, wherein a compressed hydrogen-sulfide-comprising gas stream is obtained;
ii) flushing the compressor with a mixture comprising dialkyl polysulfides, dialkyl disulfides and at least one amine;
iii) reacting the compressed hydrogen-sulfide-comprising gas stream obtained in step i) with one or more alkanols.

The steps i) and ii) have been described hereinbefore.

Step iii)

The reaction in step iii) can be carried out in this case by customary processes known those skilled in the art. Suitable processes are mentioned, for example, in DE 101 37 773 A1. Customarily, the reaction of the alkanols with the compressed hydrogen-sulfide-comprising gas stream proceeds in the presence of catalysts. Suitable catalysts are, for example, disclosed in U.S. Pat. No. 2,874,129 (metal oxides of thorium, zirconium, titanium, vanadium, tungsten, molybdenum or chromium on a porous support, for example $Al_2O_3$ or pumice); EP-A 0 749 961 (alkali metal carbonate on $Al_2O_3$); EP-A 1 005 906 (catalyst based on zirconium oxide doped with magnesium or alkaline earth metals), EP-A 0 038 540 (zeolite catalyst having a reduced amount of alkali metal cations), EP-A 0 564 706 (catalyst made of amorphous $Al_2O_3$ gel and/or made from $Al_2O_3$ gel applied to an aluminum-comprising material); U.S. Pat. No. 2,822,401 (activated $Al_2O_3$), U.S. Pat. No. 2,820,062 (active $Al_2O_3$ having 1.5 to 15% by weight of potassium tungstenate as promoter), DE 196 39 584 (active $Al_2O_3$ having 15 to 40% by weight of cesium tungstenate as promoter) and in U.S. Pat. No. 5,874,630 ($Al_2O_3$ having 0 to 20% by weight of a transition metal compound and 0.1 to 10% by weight of an alkali metal or alkaline earth metal bicarbonate, -carbonate, -oxide- or hydroxide). Preferably, use is made of catalysts based on $Al_2O_3$, particularly preferably $\gamma$-$Al_2O_3$ which is if appropriate doped with promoters. Suitable promoters are transition metal compounds selected from the group consisting of $WO_3$, $K_2WO_4$, $H_2WO_4$, $Cs_2WO_4$, $Na_2WO_4$, $MoO_3$, $K_2MoO_4$, $H_2MoO_4$, $Na_2MoO_4$, phosphotungstenate, phosphomolybdate and silicotungstenate. The fraction of the promoter is in general 1 to 40% by weight, preferably 5 to 25% by weight, based on the weight of the catalyst. In the alkylmercaptan synthesis in step iii), as catalyst, use is made particularly preferably of $\gamma$-$Al_2O_3$ which is doped with $K_2WO_4$ as promoter. Preferred alkylmercaptans have alkyl moieties having 1 to 14 carbon atoms, particularly preferably 1 to 6 carbon atoms, very particularly preferably 1 to 3 carbon atoms, that is to say methyl, ethyl, n-propyl or isopropyl moieties. Therefore, the alkanols ROH used in step iii) of the process for producing alkylmercaptans are the corresponding alkanols.

Generally, step iii) for producing alkylmercaptans is carried out as a gas phase reaction. In this case, the alkanol and the hydrogen-sulfide-comprising gas stream are customarily heated to a temperature which is sufficiently high that not only the alkanol but also the desired alkylmercaptan are present in the vapor phase. In this case, the temperature must not be selected to be so high that decomposition of the alkylmercaptan occurs. Generally, the process according to step iii) is carried out at temperatures between 250 and 500° C., preferably between 300 and 450° C. The pressure is generally 1 to 25 bar, preferably 1 to 10 bar absolute.

The resultant alkylmercaptans can be reacted directly further to give dialkyl disulfides. In addition, the alkylmercaptans can be used for producing alkanesulfonic acids.

In a preferred embodiment, the "crude mercaptan stream" which is produced using the abovementioned process, that is to say a mercaptan stream which is not purified by extraction or distillation and which can comprise incompletely reacted hydrogen sulfide, water and, as minor components, dialkyl sulfide, small amounts of alkanol and dialkyl ether, is further used for producing dialkyl disulfides.

Production of Dialkyl Disulfides

The dialkyl sulfides can be produced by any desired processes known to those skilled in the art provided that they comprise a step for compressing hydrogen-sulfide-comprising gas streams. The hydrogen-sulfide-comprising gas streams are compressed according to the process according to the invention comprising the steps i) and ii).

In a preferred embodiment, the dialkyl disulfides are produced by a process which comprises a) producing alkylmercaptans comprising the steps i), ii) and iii) which are mentioned hereinbefore, and
b) converting the alkylmercaptans obtained in step a) to dialkyl disulfides by oxidation with sulfur.

Step a)

The alkymercaptans are produced in step a) as has been described hereinbefore with respect to production of alkylmercaptans.

Step b)

When the dialkyl disulfides are produced by a process comprising the steps a) and b), in step b) the reaction of the alkylmercaptans obtained in step a) proceeds preferably with sulfur dissolved in an organic disulfide with catalysis by an amine. Suitable amines are the amines which are mentioned hereinbefore with respect to those in the mixture which is used for flushing in step ii) of the process according to the invention.

Customarily, step b) is carried out in a reaction column, wherein the low-boilers which occur are recirculated to step a).

In a preferred embodiment, step b) of the abovementioned process is followed by phase separation of the resultant mixture of aqueous phase, which is ejected, and organosulfur phase.

Subsequently, in a further preferred embodiment, the organosulfur phase is purified, which phase comprises, if appropriate, low-boilers, the desired organic disulfide, polysulfides, amine and small amounts of further by-products, wherein the organic disulfide is taken off, if appropriate low-boilers which occur are recirculated to step (a) and polysulfides which occur and amine are recirculated to step (b), with addition of sulfur and, if appropriate, amine, wherein the phase separation and the ejection of the aqueous phase can proceed subsequently to step (a) or step (b).

The organic disulfide used as solvent in step (b) is preferably the organic disulfide which is to be produced.

A particularly suitable process for producing the dialkyl disulfides is mentioned in DE 198 54 427 A1, in which in step a) the reaction of alkanols with hydrogen sulfide proceeds in the presence of a suitable catalyst to give a "crude mercaptan stream" comprising mercaptan, water, hydrogen sulfide and also small amounts of other by-products such as organic sulfide and ether, and in the subsequent step b) the reaction of the "crude mercaptan stream" with sulfur dissolved in an organic disulfide proceeds with catalysis by an amine. According to the invention, the hydrogen sulfide used in step a) is compressed according to the process comprising the steps i) and ii).

A further preferred process for producing dialkyl disulfides is disclosed in DE 101 16 817 A1, in which the production of organic disulfides in a column equipped with temperature-controllable trays from a crude mercaptan stream without prior separation by distillation is mentioned. According to the invention, the hydrogen sulfide is compressed by a process comprising the steps i) and ii) which are mentioned hereinbefore.

Production of Alkanesulfonic Acids

The present invention further relates to a process for producing alkanesulfonic acids, which is likewise carried out starting from hydrogen-sulfide-comprising gas streams which are compressed according to the invention.

Suitable processes for producing alkanesulfonic acids starting from compressed hydrogen sulfide gas streams are known to those skilled in the art.

In a preferred embodiment, the alkanesulfonic acids are produced by a process which comprises a) producing alkylmercaptans by a reaction with alkanols with a gas stream which is compressed according to the compression process according to the invention comprising the steps i) and ii);
b) converting the mercaptans produced in step a) to dialkyl disulfides by oxidation with sulfur; and
c) oxidizing the dialkyl disulfides obtained in step b) to alkanesulfonic acid using an oxidizing agent.

The steps a) and b) correspond in this case to the steps a) and b) mentioned with respect to the production of dialkyl disulfides.

The oxidation in step c) can be achieved using various oxidizing agents. For instance, the oxidizing agents used can be hydrogen peroxide, chlorine, dimethyl sulfoxide, mixtures of dimethyl sulfoxide and hydroiodic acid and also nitric acid or mixtures of said oxidizing agents. In addition, electrochemical oxidation is possible. Suitable processes for producing alkanesulfonic acids by oxidizing the corresponding dialkyl disulfides are known to those skilled in the art and are disclosed, for example, in WO 98/34914, U.S. Pat. No. 2,697,722, U.S. Pat. No. 2,727,920 and WO 00/31027.

It is essential in the case of the abovementioned processes for producing sulfur compounds, selected from alkylmercaptans, dialkyl disulfides and alkanesulfonic acids, that this process comprises a step for compressing a hydrogen-sulfide-comprising gas stream, wherein the compression of the hydrogen-sulfide-comprising gas stream is carried out in accordance with the process according to the invention comprising the steps i) and ii).

In a particularly preferred embodiment, the present invention relates to a process for producing dialkyl disulfides, in particular a process for producing dialkyl disulfides which comprises the steps (a) and (b) as listed hereinbefore.

The compressor in the process according to the invention for producing dialkyl disulfides is preferably flushed with a mixture comprising dialkyl disulfides, dialkyl polysulfides and at least one amine, wherein this mixture is the amine-comprising crude discharge from the dialkyl disulfide synthesis. In this case, preferred compositions of the crude discharge are mentioned hereinbefore for discontinuous flushing or continuous flushing in each case. The mixture used for the flushing can, after the flushing in step ii) of the process according to the invention, be recirculated back to the process for producing dialkyl disulfides, generally to the bottom phase of the dialkyl disulfide purifying distillation (preferably in the discontinuous flushing process in step ii)) or to the bottom phase of the dialkyl disulfide reaction column after removal of the aqueous phase (preferably in the continuous flushing process in step ii)).

In FIG. 1, a process diagram is presented in which the production of dialkyl disulfides is shown. The symbols herein have the following meanings:

$H_2S$ feed of the hydrogen-sulfide-comprising gas stream
ROH feed of alkanol
V compressor
A reactor for producing alkylmercaptan
B reactor for producing dialkyl disulfide, customarily dialkyl disulfide reaction column
$S_8$ feed of elemental sulfur
NRR' feed of amine
C phase separator
D dialkyl disulfide distillation column, customarily dialkyl disulfide purifying distillation column
$H_2O$ takeoff of the aqueous phase
P product takeoff (pure dialkyl disulfide)
Pu ejection stream for avoidance of accumulation (Purge)

The symbols x and xx indicate at what points the amine-comprising crude discharge is preferably taken off for flushing in step ii) of the compression process according to the invention. In this case, the point designated x shows the takeoff point from the bottom phase of the dialkyl disulfide purifying distillation, i.e. of the mixture which is preferably used for the discontinuous flushing, and the point designated xx shows the takeoff point from the bottom phase of the dialkyl disulfide reaction column after removal of the aqueous phase, i.e. of the mixture which is preferably used for continuous flushing.

It is clear from the process diagram in FIG. 1 that the mixture which is preferably used for discontinuous flushing in step i) of the compression process preferably corresponds to the bottom phase of the dialkyl disulfide purifying distillation from the last column D of the dialkyl disulfide synthesis. The mixture which is preferably used for the continuous flushing in step ii) of the compression process according to the invention preferably corresponds to the bottom phase from column B after phase separation in the phase separator C, wherein the aqueous phase is separated off and the organic phase is used for flushing.

An essential advantage of the process according to the invention is that the mixture used for flushing the compressor need not be produced in a complex manner, but corresponds to the amine-comprising crude discharge from the dialkyl disulfide synthesis. This is an advantage, in particular, when the compressed hydrogen-sulfide-comprising gas stream is used for the production of dialkyl disulfides.

The hydrogen-sulfide-comprising gas which is passed through the compressor in the production of the abovementioned sulfur compounds does not generally correspond to the pure hydrogen-sulfide-comprising gas stream which is used at the start of the process but is a circulated gas which customarily comprises 60 to 90% by weight, preferably 70 to 80% by weight, of hydrogen sulfide, 2 to 20% by weight, preferably 5 to 15% by weight, of dimethyl sulfide and also small amounts of carbon monoxide, methylmercaptan and dimethyl ether.

The present invention further relates to the use of a mixture comprising dialkyl polysulfides, dialkyl disulfides and at least one amine for removing sulfur deposits which occur in the compression of hydrogen-sulfide-comprising gas streams. These sulfur deposits occur in this case generally in the compressor, wherein compressor is taken to mean not only the compressor itself but also its peripherals—as listed hereinbefore. Mixtures which are preferably used and also compression processes which are preferably carried out are mentioned hereinbefore.

The examples hereinafter additionally describe the invention.

EXAMPLES

The examples are carried out in each case using a liquid ring compressor having a plate heat exchanger for cooling the ring liquid and possibility for bypass, which compressor has sulfur deposits from compression operations carried out on H$_2$S which originates from the synthesis from the elements and is used in a process for the synthesis of methylmercaptan. The sulfur deposits are identical in the examples and comparative examples.

1. Comparative Example

Discontinuous Flushing

For the discontinuous flushing, the compressor and peripherals thereof are shut off and filled with dimethyl disulfide which is known as a good solvent for sulfur. The compressor, after an exposure time of 30 minutes, at a temperature of 90° C., is free for further operation of 3 weeks.

2. Example According to the Invention

Discontinuous Flushing

As in example 1, the compressor and peripherals thereof are shut off. Instead of dimethyl disulfide, the compressor, however, is filled with a polysulfide solution from the bottom phase of the dimethyl disulfide purifying distillation. For this, the compressor and peripherals thereof are filled with the bottom phase discharge. After an exposure time of 30 minutes at a temperature of 90° C., compressor and peripherals thereof are free for further operation of the plant of 3 months. The flushing liquid is recirculated to the bottom phase of the dimethyl disulfide purifying distillation.

3. Example According to the Invention

Continuous Flushing

For the continuous flushing, the organic phase from the phase separator downstream of the dimethyl disulfide crude column is used. For this, 0.5 to 10 kg, preferably 1 to 5 kg, of organic phase are taken off from the phase separator per 100 kg of hydrogen sulfide which is to be compressed and fed into the compressor on the suction side or the ring liquid feed when a liquid ring compressor is used. The liquid phase which is separated off downstream of the compressor is preferably recirculated to the bottom phase of the dimethyl disulfide reaction column.

The invention claimed is:

1. A process for compressing a hydrogen-sulfide-comprising gas stream, the process comprising
    (i) compressing the hydrogen-sulfide-comprising gas stream in a compressor,
    (ii) flushing the compressor with a mixture comprising
        a) 10 to 98% by weight of at least one dialkyl polysulfide,
        b) 1.9 to 80% by weight of at least one dialkyl disulfide, and
        c) 0.1 to 10% by weight of at least one amine,
    wherein a sum of dialkyl polysulfides, dialkyl sulfides and amines totals 100% by weight,
    wherein an entry pressure into the compressor is from 700 mbar to 3000 mbar absolute, and an exit pressure from the compressor is from 1000 to 7000 mbar absolute, with the proviso that the entry pressure is lower than the exit pressure, and
    wherein an entry temperature into the compressor is from 10 to 70° C., and an exit temperature from the compressor is from 15 to 200° C., with the proviso that the entry temperature is lower than the exit temperature.

2. The process of claim 1, wherein the compressor is a rotary gas compressor.

3. The process of claim 1, wherein the compressing (i) proceeds in one or two stages.

4. The process of claim 1, wherein the flushing (ii) proceeds continuously.

5. The process of claim 1, wherein the flushing (ii) proceeds discontinuously.

6. The process of claim 5, wherein the flushing of the compressor (ii) proceeds at a temperature in a range of 30 to 160° C.

7. The process of claim 1, wherein the mixture employed for the flushing in (ii) comprises
  a) 20 to 95% by weight of at least one dialkyl polysulfide;
  b) 4.8 to 72% by weight of at least one dialkyl disulfide;
  c) 0.2 to 8% by weight of at least one amine;
  wherein a sum of dialkyl polysulfides, dialkyl disulfides and amines totals 100% by weight.

8. The process of claim 1, wherein the hydrogen-sulfide-comprising gas stream is obtained by producing hydrogen sulfide from the elements sulfur and hydrogen.

9. A process for producing at least one selected from the group consisting of an alkylmercaptan, a dialkylsulfide, and an alkyl sulfonic acid, the processing comprising:
  compressing a hydrogen-sulfide-comprising gas stream by the method of claim 1;
  and subsequently reacting the compressed hydrogen-sulfide-comprising gas stream to obtain the at least one selected from the group consisting of an alkylmercaptan, a dialkylsulfide, and an alkyl sulfonic acid.

10. The process of claim 9, wherein the at least one alkylmercaptan is produced, and the reacting comprises reacting at least one alkanol with the compressed hydrogen-sulfide-comprising gas stream.

11. The process of claim 9, wherein the at least one dialkyl disulfide is produced, and the reacting comprises:
  a) producing at least one alkylmercaptan by reacting at least one alkanol with the compressed hydrogen-sulfide-comprising gas stream; and
  b) converting the at least one alkylmercaptan obtained in a) to at least one dialkyl disulfide by oxidizing the alkylmercaptan with sulfur.

12. The process of claim 9, wherein the at least one alkanesulfonic acid is produced, and the reacting comprises:
  a) producing at least one alkylmercaptan by reacting at least one alkanol with the compressed hydrogen-sulfide-comprising gas stream;
  b) converting the at least one alkylmercaptan produced in a) to at least one dialkyl disulfide by oxidizing the alkylmercaptan with sulfur; and
  c) oxidizing the dialkyl disulfide obtained in b) to the at least one alkanesulfonic acid with an oxidizing agent.

13. A method of removing at least one sulfur deposit produced in compressing a hydrogen-sulfide-comprising gas stream, the method comprising:
  contacting a mixture comprising at least one dialkyl polysulfide, at least one dialkyl disulfide, and at least one amine with the sulfur deposit.

14. The process of claim 1, wherein the compressor is a liquid ring compressor.

15. The process of claim 1, wherein the compressor is a screw compressor.

16. The process of claim 2, wherein the compressing (i) proceeds in one or two stages.

17. The process of claim 2, wherein the flushing (ii) proceeds continuously.

18. The process of claim 3, wherein the flushing (ii) proceeds continuously.

19. The process of claim 2, wherein the flushing (ii) proceeds discontinuously.

20. The process of claim 3, wherein the flushing (ii) proceeds discontinuously.

* * * * *